(12) United States Patent
Sklavos

(10) Patent No.: US 8,348,883 B2
(45) Date of Patent: Jan. 8, 2013

(54) DEVICE FOR IMPLANTING OBJECTS INTO ANIMAL TISSUE

(76) Inventor: Martha Sklavos, Frederick, MD (US)

( * ) Notice: Subject to any disclaimer, the term of this patent is extended or adjusted under 35 U.S.C. 154(b) by 422 days.

(21) Appl. No.: 12/570,089

(22) Filed: Sep. 30, 2009

(65) Prior Publication Data

US 2011/0077617 A1    Mar. 31, 2011

(51) Int. Cl.
*A61M 31/00*    (2006.01)
(52) U.S. Cl. ......................................................... 604/60
(58) Field of Classification Search ............... 604/57–64
See application file for complete search history.

(56) References Cited

U.S. PATENT DOCUMENTS 6,592,508 B1 *    7/2003    Ravins et al. ..................... 600/8

\* cited by examiner

Primary Examiner — Kevin C Sirmons
Assistant Examiner — Bradley Osinski

(57) ABSTRACT

A device for implanting an object into animal tissue and a method for using the same device is provided. The device includes a cannula having a longitudinal axis, a passageway extending therethrough, a proximal end, and an opposite distal end that is insertable into tissue and defines an exit aperture for discharge of the object from the cannula. The device also includes an axially movable plunger disposed and oriented in a non-coaxial relationship within at least a portion of the cannula and a partial barrier disposed within the cannula adjacent to its distal end and configured to at least partially block the passageway, where the partial barrier at least partially defining an object receiving opening that is in communication with the passageway and sufficiently sized to receive the object and the plunger. When the device is in a first position, the partial barrier prevents the object from entering the passageway even when the plunger is inserted into the object receiving opening. When the device is moved to a second position, the passageway is aligned with the object, such that, upon movement of the plunger towards the distal end of the cannula, the plunger engages the object and pushes it through the object receiving opening towards and through the exit aperture.

20 Claims, 3 Drawing Sheets

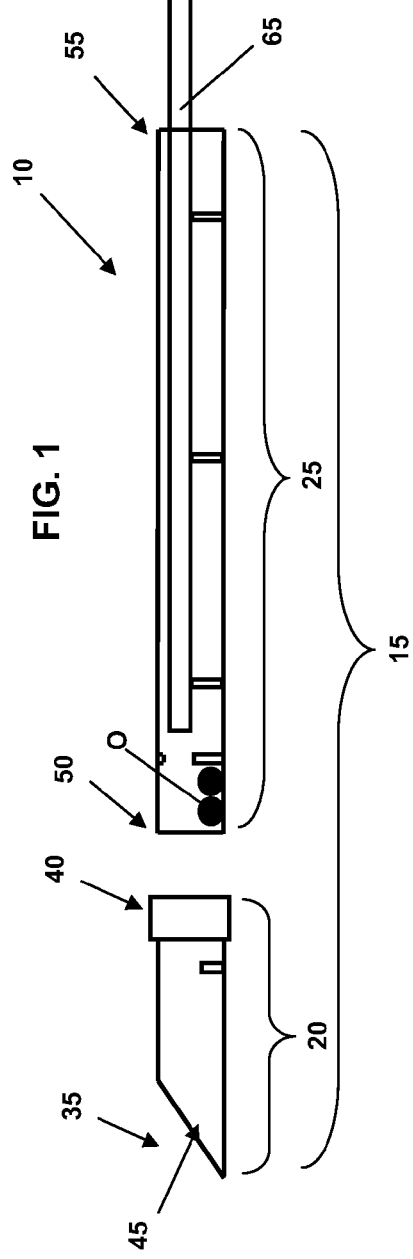
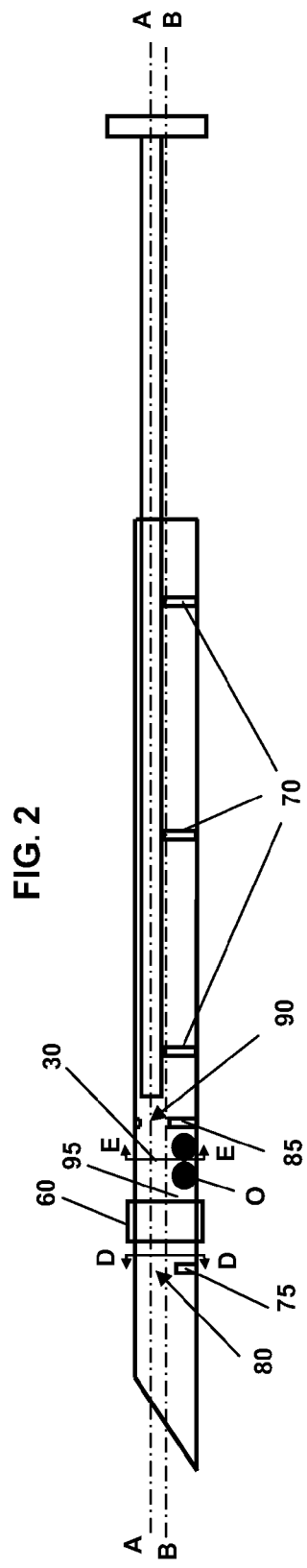

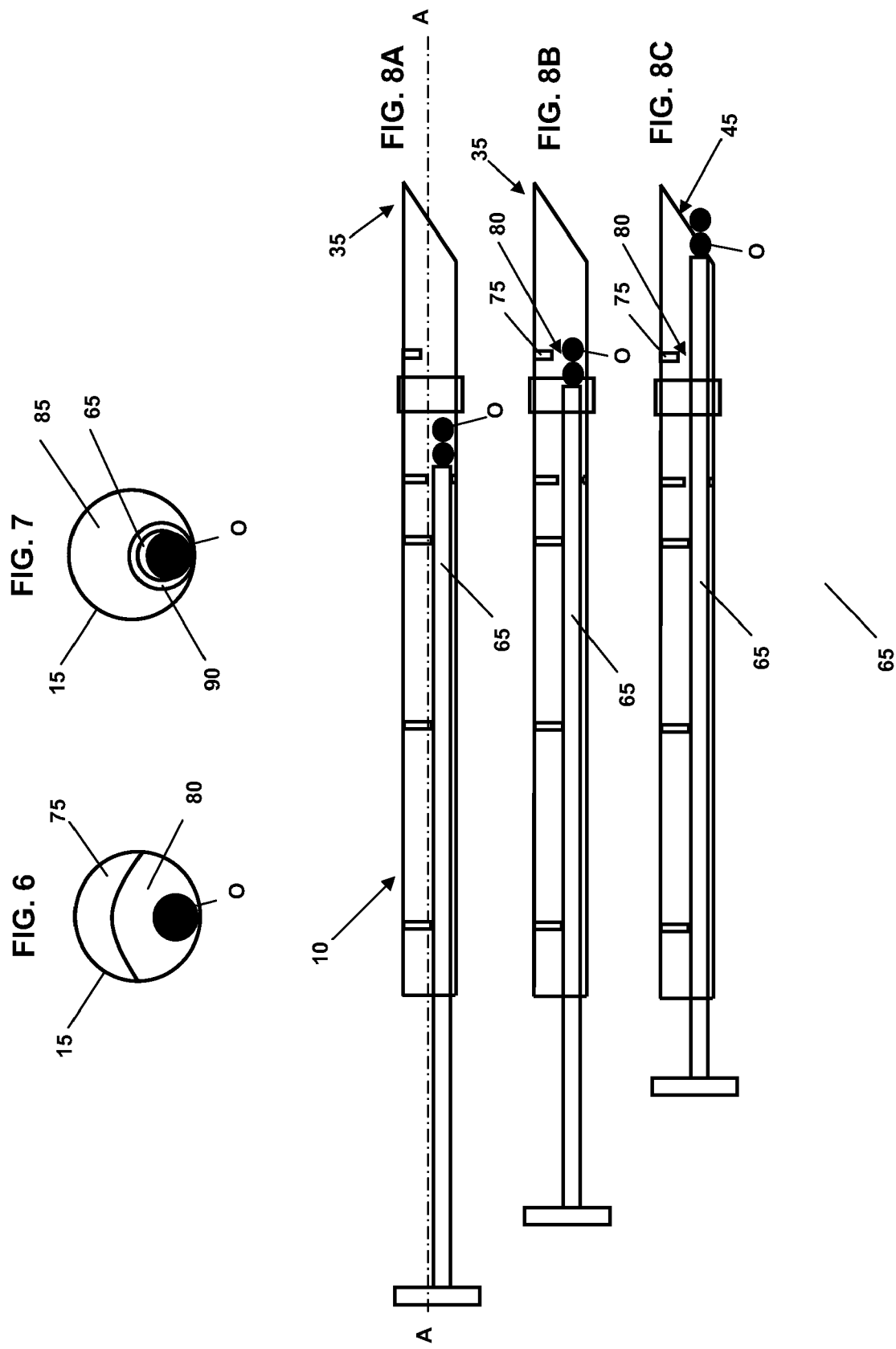

DEVICE FOR IMPLANTING OBJECTS INTO ANIMAL TISSUE

BACKGROUND

1. Field of the Invention

The present application relates to a device for implanting objects and, more particularly, to a device for implanting objects into animal tissue.

2. Description of the Related Art

There is growing interest in biomedical research for applications of sustained-release pellets, which are implanted subdermally as an alternative method of daily or multi-weekly drug injection/administration. Daily injections ensure daily stress and pain for the research subject while increasing the workload for the researcher. Current methods of liquid substance (drug) delivery by injections fail to hold the research subject at a constant therapeutic dose due to peaks and troughs associated with injections. Fortunately, sustained-release pellets are presently used in research animals, household pets, and food-producing farm animals.

A few classifications of drugs that are currently manufactured for use in sustained-release pellet form include antibiotics, steroidal and non-steroidal anti-inflammatories, other analgesics, hormones, and antioxidants. Companies, such as Innovative Research of America, customize pellets for research use based on shape, size, dosing, release rates, and length of study, thus benefiting the researcher and research subject by replacing multiple injections with less frequent subdermal pellet implants.

A trocar (http://www.innovrsrch.com/trochar.asp) is the device currently used for pellet implantation in rodents. However, the trocar can be difficult to use (often requiring two people for successful execution into a research animal), inaccurate, and non-sterile. The major difficulty with the trocar is that it lacks a mechanism to hold the pellet in a secure and sterile manner during pellet implantation. Pellet implantation using the trocar often requires multiple attempts due to dulling of the device with repeated use, which can result in failure to break the skin, poor pellet placement, and the pellet falling out of the device and into the bacteria-covered coat hair of the animal. Due to the complications of this procedure, one must restrain the animal repeatedly, sometimes leading to multiple incisions due to inaccuracy of pellet implantation and lack of device control, which can contribute to an increase in subcutaneous nonspecific inflammation for the research subject and holds potential to falsify the true outcome of the research study.

Kersco's U.S. Pat. No. 4,105,030 describes an intricate delivery device for implanting multiple pellets. Though multiple pellets can be loaded into the gun-like device and held in the device with a valve until delivery, multiple pellets cannot be implanted at one time as individual pellets must be forced through a slit in the valve. Kersco's slit design also subjects the pellets to compression stress thereby compromising the integrity of the pellet(s). Additionally, the bulk and proportion of the device, with respect to a small animal research subject, may be difficult to maneuver and operate resulting in an exertion of unnecessary force on the subject thereby leading to poor pellet placement or injury to the animal.

U.S. Pat. No. 5,810,769 to Schlegel (1998) and U.S. Pat. No. 5,281,197 to Arias (1994) aimed to correct problems arising from a device whose pellet(s) cannot be restrained before the desired time of implantation. These patents suggested decreasing the diameter of the cannula and increasing the diameter of the pellet so that the pellet is held in the device until it is forced through the cannula. Unfortunately, solving one problem has created another in that the integrity of the pellet(s) is now subject to degradation. A pellet with a diameter larger than the cannula is mechanically forced through the cannula, and therefore, a portion of the substance to be delivered into the subject, is lost to compression strain. Schlegel notes that this type of pellet restraining mechanism requires pellets with elastic properties as not to compromise the contents of the pellet. If the pellets are not of an exact size, with a diameter barely larger than the narrowed cannula, there is a risk for device failure, specifically if the pellets are too small in diameter and they cannot be contained within the narrowed portion of the cannula, or, conversely, if the pellet diameter is so large that the pellets cannot be mechanically forced through the narrowed cannula without excessive damage to the integrity of a pellet with, and especially, without, elastic properties. Essentially, Schlegel's device is limiting in application and use of as the device requires inserted objects to contain elastic properties or be uncompromised by compression strain.

Another patent of similar interest is U.S. Pat. No. 7,104,945 to Miller (2006). Miller's device is intended to improve upon previous strategies to retain an object in the delivery device prior to implanting the pellet into tissue without the use of bone wax. Specifically, the pellet and spacers (brachytherapy procedure) are held by flexible tabs and are forced passed the tabs to allow the pellet to pass into the tissue. This device can hold multiple objects, however each implantation yields a decrease in mechanical function as tabs are flexed multiple times leading to an increasing margin of error and a decrease in function and accuracy (and timing) of delivery. In Miller's device, the spacers appear to be significantly larger in diameter than the seeds, which raises the concern of the spacers compromising the integrity of the flexible tab to the extent that the comparatively smaller pellet can no longer be contained using the tab, resulting in failure of the retaining mechanism and inaccurate delivery of the pellet. Conversely, if the retaining tab is too stringent, the tab, itself, could compromise the contents of the pellet, especially if the pellet does not posses elastic properties to avoid damage incurred from the compression strain of forcing the pellet passed the tab.

Prior devices capable of retaining an object in a device to maintain control of the object prior to reaching the desired site of implantation have overcomplicated the function of the device and/or included a counterproductive mechanism which can alter the integrity of the object's contents upon implantation. Consequently, there exists a need for a device that can efficiently and effectively deliver objects into subjects without damaging the objects or decreasing effectiveness when delivering more than one object per procedure.

SUMMARY

In one embodiment, a device for implanting an object into animal tissue is provided. The device includes a cannula having a longitudinal axis, a passageway extending therethrough, a proximal end, and an opposite distal end that is insertable into tissue and defines an exit aperture for discharge of the object from the cannula. The device also includes an axially movable plunger disposed and oriented in a non-coaxial relationship within at least a portion of the cannula and a partial barrier disposed within the cannula adjacent to its distal end and configured to at least partially block the passageway, where the partial barrier at least partially defining an object receiving opening that is in communication with the passageway and sufficiently sized to receive the object and the plunger. When the device is in a first position, the partial barrier prevents the object from entering the passageway even when the plunger is inserted into the object receiving opening. When the device is moved to a second position, the passageway is aligned with the object, such that, upon movement of the plunger towards the distal end of the cannula, the plunger engages the object and pushes it through the object receiving opening towards the exit aperture.

In another embodiment, a device for implanting an object into animal tissue is provided. The device includes a cannula including first and second portions that are connectable to and separable from each other, a longitudinal axis when the first and second portions are connected together, and a passageway extending therethrough. The first portion has a proximal end and an opposite distal end that is insertable into tissue and defines an exit aperture for discharge of the object from the cannula. The device further includes an axially movable plunger disposed and oriented in a non-coaxial relationship within at least a portion of the cannula; a first partial barrier disposed within the first portion of the cannula and configured to at least partially block the passageway, where the first partial barrier at least partially defining an object receiving opening that is in communication with the passageway and sufficiently sized to receive the object and the plunger; and a second partial barrier disposed within the second portion of the cannula and configured to form a temporary storage space between the first partial barrier and the second partial barrier when the first and second portions are connected together, where the second partial barrier at least partially defining a plunger receiving opening that is in communication with the passageway and sufficiently sized to receive the plunger, but prevent the object from entering therein. When the device is in a first position, the first partial barrier prevents the object from entering the passageway even when the plunger is inserted into the object receiving opening. When the device is moved to a second position, the passageway is aligned with the object, such that, upon movement of the plunger towards the distal end of the first portion of the cannula, the plunger engages the object and pushes it through the object receiving opening of the first partial barrier towards the exit aperture of the first portion of the cannula.

In another embodiment, a method for implanting an object into animal tissue is provided. The method includes the steps of providing a device that includes a cannula having a longitudinal axis, a passageway extending therethrough, a proximal end, and an opposite distal end that defines an exit aperture for discharge of the object from the cannula; an axially movable plunger disposed and oriented in a non-coaxial relationship within at least a portion of the cannula; and a partial barrier disposed within the cannula adjacent to its distal end and configured to at least partially block the passageway, the partial barrier at least partially defining an object receiving opening that is in communication with the passageway and sufficiently sized to receive the object and the plunger. The method further includes the steps of loading the cannula with the object; orienting the device to a position where the partial barrier prevents the object from entering the passageway; inserting the distal end of the cannula into the animal tissue; rotating the device about the longitudinal axis of the cannula to align the object with the object receiving opening due to the effect of gravity; and moving the plunger towards the distal end of the cannula to push the object through the passageway until it exits the exit aperture.

BRIEF DESCRIPTION OF THE DRAWINGS

It will be appreciated that the illustrated boundaries of components in the figures represent one example of the boundaries. One of ordinary skill in the art will appreciate that one component may be designed as multiple components or that multiple components may be designed as one component. Additionally, an internal component may be implemented as an external component and vice versa.

Further, in the accompanying drawings and description that follow, like parts are indicated throughout the drawings and description with the same reference numerals, respectively. The figures may not be drawn to scale and the proportions of certain parts have been exaggerated for convenience of illustration.

FIG. 1 illustrates a longitudinal cross-sectional view of one embodiment of a device 10 for implanting objects into animal tissue, where the device is in its uncoupled position and in its starting position.

FIG. 2 illustrates a longitudinal cross-sectional view of the device 10 in its coupled position.

FIG. 6 illustrates an enlarged cross-sectional view of the device 10 taken along line F-F with an object O loaded in the device 10.

FIG. 7 illustrates an enlarged cross-sectional view of the device 10 taken along line G-G with an object O loaded in the device 10.

FIGS. 8A-8C illustrate longitudinal cross-sectional views of the device 10 at various stages during the object implantation process.

DETAILED DESCRIPTION

Figure 3A:
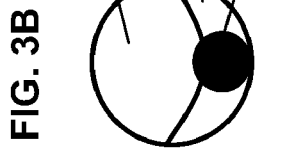
FIG. 3A illustrates an enlarged cross-sectional view of the device 10 taken along line D-D without an object O loaded in the device 10.

Illustrated in FIG. 1 is a longitudinal perspective view of one embodiment of a device 10 for implanting objects O into animal tissue. The objects O can include, for example, sustained-release drug pellets that are spherical in shape as shown in the figures. In other embodiments (not shown), the objects can be drug pellets taking the form of other shapes such as egg-shaped, cylindrical, spherical, and triangular. In other embodiments (not shown), the objects can include seeds, tablets, fragments, or pellets that take the form of a variety of shapes.

The device 10 includes a cannula 15 having a distal portion 20 (which may also referred to as "the first portion 20") that is configured to be coupled to and separable from a second portion 25 (which may also be referred to as "the second portion 25"). As shown in FIG. 1, the distal and proximal portions 20, 25 are disconnected from each other, such that the device 10 is in its uncoupled position. When the device 10 is in its uncoupled position, objects O can be loaded into the cannula 15. In an alternative embodiment (not shown), the cannula may take the form of a single-piece construction, so long as the cannula is configured to permit loading of objects therein. For example, the cannula can include an opening or port to permit loading of the objects therethrough.

Illustrated in FIG. 2 is a longitudinal perspective view of the device 10 in its coupled position where the first and second portions 20, 25 are connected to each other. When the device 10 is in its coupled position, the distal and proximal portions 20, 25 of the cannula 15 define a passageway 30 therethrough and share the same central longitudinal axis A (which is also the longitudinal axis of the device 10).

The distal portion 20 of the cannula 15 includes a distal end 35 (which may also referred to as "the distal end 35 of the cannula 15") that is configured for insertion into animal tissue and a proximal end 40. In the illustrated embodiment, the distal end 35 of the distal portion 20 includes a beveled tip that defines an exit aperture 45 for discharge of the objects O from the cannula 15. The proximal portion 25 of the cannula 15 includes a distal end 50 that is configured to connect to the proximal end 40 of the distal portion 20 of the cannula 15 and a proximal end 55 (which may also referred to as "the proximal end 55 of the cannula 15"). In the illustrated embodiment, a connector 60 is employed to enable the distal end 50 of the proximal portion 25 to be coupled to and separated from the proximal end 40 of the distal portion 20. In one embodiment, the connector includes a threaded connector such as a luer-style connector. In another embodiment (not shown), the distal end 50 of the proximal portion 25 of the cannula 15 can be coupled to the proximal end 40 of the distal portion 20 of the cannula 15 via a friction fit, instead of using a connector.

In the illustrated embodiment, the cannula 15 has a circular cross-section. In alternative embodiments (not shown), the cannula can have a square cross-section, triangular cross-section, or any other suitable shape.

The device 10 further includes an axially movable plunger 65 that is disposed within at least a portion of the cannula 15 and configured to engage one of the objects O and push it towards the distal end 35 of the cannula 15. As shown in FIG. 2, the plunger 65 has a central longitudinal axis B that is offset from the central longitudinal axis A of the cannula 15. In other words, the plunger 65 is oriented in a non-coaxial relationship within the cannula 15.

To assist in guiding the axial movement of the plunger 65 within the cannula 15, the proximal portion 25 of the cannula 15 includes guides 70. In one embodiment, the guides 70 may be integral with the proximal portion 25 of the cannula 15. In another embodiment, the guides may be separate pieces that are connected to an inner surface of the cannula 15.

With continued reference to FIG. 2, the distal portion 20 of the cannula 15 includes a first partial barrier 75 configured to at least partially block the passageway 30 to prevent objects O from exiting the exit aperture 45 when the device 10 is oriented in a position (which may be referred to as the "first position" or the "starting position") where the first partial barrier 75 generally faces the ground (the device 10 in FIG. 2 is in its starting position). It will be appreciated that the device 10 can be oriented at an angle relative to the ground, yet still be in the starting position, so long as the first partial barrier 75 is facing towards the ground.

Figure 5:
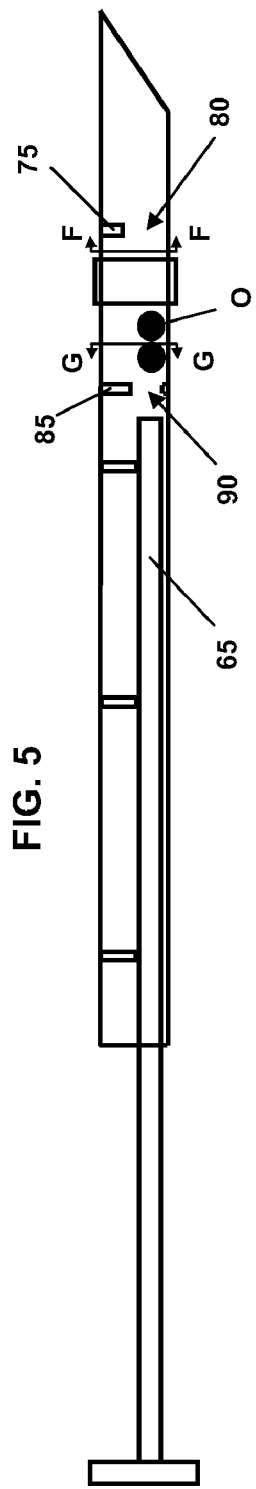
FIG. 5 illustrates a longitudinal cross-sectional view of the device 10 in its coupled position and in its implanting position.

The first partial barrier 75 at least partially defines an object receiving opening 80 that is in communication with the passageway 30. The object receiving opening 80 is sufficiently sized to receive the objects O, such that when the device 10 is moved to a different position (which may be referred to as the "second position" or the "implanting position") (see FIG. 5) where the first partial barrier 75 generally faces away from the ground (e.g., through rotation of the device 10 approximately 180 degrees about the longitudinal axis A), the objects O generally align with the object receiving opening 80 due to the effect of gravity and are permitted to pass therethrough in response to urging of the plunger 65. It will be appreciated that the device 10 can be oriented at an angle relative to the ground, yet still be in the implanting position, so long as the first partial barrier 75 is facing away from the ground.

Figure 3B:
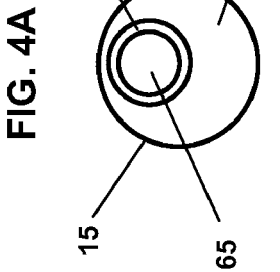
FIG. 3B illustrates an enlarged cross-sectional view of the device 10 taken along line D-D with an object O loaded in the device 10.

In the illustrated embodiment, as shown in FIGS. 3A and 3B, the first partial barrier 75 is crescent-shaped. In alternative embodiments (not shown), the first partial barrier 75 may take the form of any other shape, such as semicircular-shaped, "V"-shaped, or a circular segment, so long as it is sufficiently sized and shaped to prevent objects O from exiting the exit aperture 45 when the device 10 is oriented in its starting position and the resulting object receiving opening 80 is sufficiently sized and shaped to permit object O to pass therethrough in response to urging of the plunger 65 when the device 10 is moved to its implanting position. In one embodiment, the first partial barrier 75 may be integral with the cannula 15. In another embodiment, the first partial barrier 75 may be a separate component that is connected to an inner surface of the cannula 15.

With reference back to FIG. 2, the proximal portion 25 of the cannula 15 includes a second partial barrier 85 that is configured to at least partially block the passageway 30 to prevent objects O from moving past the second partial barrier 85 towards the proximal end 55 of the cannula 15, when the device 10 is in its starting position. The second partial barrier 85 at least partially defines a plunger receiving opening 90 that is in communication with the passageway 30. The plunger receiving opening 90 is sufficiently sized to receive the plunger 65, but prevent the objects O from entering therethrough, when the device 10 is moved to its implanting position. As shown in FIG. 2, the second partial barrier 85 is axially spaced from the first partial barrier 75 when the device 10 is in its coupled position, thereby forming a temporary space 95 to house the objects O.

Figure 4A:
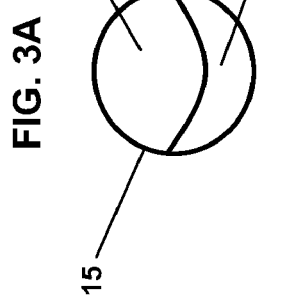
FIG. 4A illustrates an enlarged cross-sectional view of the device 10 taken along line E-E without an object O loaded in the device 10.
Figure 4B:
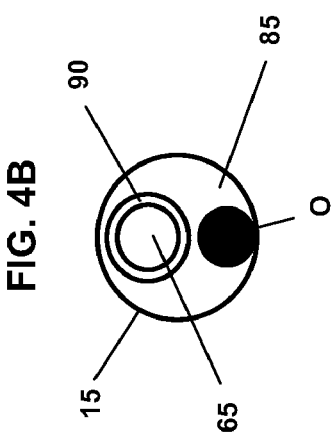
FIG. 4B illustrates an enlarged cross-sectional view of the device 10 taken along line E-E with an object O loaded in the device 10.

In the illustrated embodiment, as shown in FIGS. 4A and 4B, the second partial barrier 85 and the plunger receiving opening 90 are circular-shaped. In alternative embodiments (not shown), the second partial barrier 85 and the plunger receiving opening 90 may take the form of any other shape, such as semicircular-shaped, "V"-shaped, or a circular segment, so long as the second partial barrier 85 is sufficiently sized and shaped to prevent objects O from moving past the second partial barrier 85 towards the proximal end 55 of the cannula 15 when the device 10 is in its starting position, and the plunger receiving opening 90 is sufficiently sized and shaped to receive the plunger 65, but prevent the objects O from entering therethrough when the device 10 is moved to its implanting position. In one embodiment, the second partial barrier 85 may be integral with the cannula 15. In another embodiment, the second partial barrier 85 may be a separate component that is connected to an inner surface of the cannula 15.

In one embodiment, the distal portion 20 of the cannula 15 is constructed of a metal material (e.g., stainless steel), and the proximal portion 25 of the cannula 15 and the plunger 65 are constructed from a polymeric material or glass, which is inert and biologically safe, or any combination of the these materials, so that it can be disposable or reusable. In another embodiment, both portions of the cannula 15 and the plunger 65 can be constructed from a suitable polymeric material, so the entire device 10 can be disposable. In yet another embodiment, both portions of the cannula 15 and the plunger 65 can be constructed from a suitable metallic material (e.g., stainless steel), so that the entire device 10 can be reusable.

To use the device 10, objects O are first loaded into the cannula 15 by separating the distal and proximal portions 20, 25 of the cannula 15 from each other (i.e., to configure the device 10 in its uncoupled position, FIG. 1) and then inserted into the distal portion 20 of the cannula 15 until they rest against the first partial barrier 75. Optionally, the objects O can be inserted into the proximal portion 25 until they rest against the second partial barrier 85. The distal and proximal portions 20, 25 of the cannula 15 are then coupled to each other (i.e., to configure the device 10 in its coupled position, FIG. 2), so that the objects O are trapped in the temporary space 95 of the cannula 15 between the first and second partial barriers 75, 85, when the device 10 is in its starting position.

With the device 10 loaded, the operator then orients the device 10 to the starting position where the first partial barrier 75 prevents the object from entering the passageway 30 and exiting through the exit aperture 45 (FIG. 2). While in this position, the distal end 35 of the cannula 15 is inserted into the animal tissue. Next, the device 10 is rotated about its longitudinal axis A to its implanting position (FIG. 8A) to align the objects O with the object receiving opening 80 (FIG. 6) and the plunger 65 (FIG. 7) due to the effect of gravity. While in this position, the operator then moves the plunger 65 axially towards the distal end 35 of the cannula 15 to push the objects O through the object receiving opening 80 (FIG. 8B) until they exit the exit aperture 45 of the cannula 15 (FIG. 8C).

The present invention shall be more concretely explained with the following example, which is to be considered merely representative of the present invention and thus should not be considered as limiting.

EXAMPLE

A device similar to the device 10 described above and illustrated in the figures can be used to implant drug pellets in a rodent to conduct drug studies. In this example, the operator would first load the drug pellets into the device in the manner described above. With the device loaded, the operator would then restrain the rodent so that the area where the pellet is to be implanted (usually the scruff of the neck) is exposed. Next, the operator would orient the device to its starting position and then insert the beveled tip of the cannula under the rodent's skin, but above its muscle, to the desired insertion location. To allow the pellet to be implanted into the rodent, the device would then be rotated to its implanting position to allow the pellet(s) to drop and align with the object receiving opening, due to the effect of gravity, so that they are no longer obstructed by the first partial barrier. At this time, the pellet(s) can be inserted into the rodent by pushing on the plunger, which guides the pellet(s) through the cannula and into the desired implantation location. After the pellet(s) has/have been implanted, the operator would then remove the device from under the rodent's skin much like after an injection is administered with a syringe.

There are several potential advantages to the device 10 described above and illustrated in the figures and all of the alternative embodiments described herein. First, the operator can restrain the rodent or other test animal with one hand (or with the help of a restrainer) and implant the pellet in a manner similar to the method used to inject liquid via a syringe. This method of pellet implantation can allow one person to implant a pellet into a rodent or test animal efficiently, sterily, with greater ease, accuracy and limited restraint time, while inflicting less pain, suffering, and stress on the rodent or test animal. Second, the device 10 and all of the alternative embodiments described herein can deliver a pellet in a similar manner to liquids administered via a syringe as syringes are increasingly accurate and user-friendly, allowing one person to efficiently administer the substance to a subject or to themselves. Third, the device 10 and all of the alternative embodiments described herein can be readily and inexpensively manufactured.

It will be appreciated that the device 10 and all of the alternative embodiments described herein has applicability in several fields including clinical practice in humans (e.g., brachytherapy), veterinary care, tracking pets, wildlife/endangered species, zoo animals, livestock, and farm animals, and especifically in the area of small animal research. Further, it will be appreciated that the dimensions of the device 10 and all of the alternative embodiments described herein can be modified to accommodate different pellet sizes and shapes and the number of pellets to be delivered at one time.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or multiple components.

While the present application illustrates various embodiments, and while these embodiments have been described in some detail, it is not the intention of the applicant to restrict or in any way limit the scope of the claimed invention to such detail. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's claimed invention. Moreover, the foregoing embodiments are illustrative, and no single feature or element is essential to all possible combinations that may be claimed in this or a later application.

What is claimed is:

1. A device for implanting an object into animal tissue, the device comprising:

a cannula having a proximal end, an opposite distal end that is insertable into tissue and defines an exit aperture for discharge of the object from the cannula, and a passageway extending from the proximal end to the distal end, all of which share the same longitudinal axis;

an axially movable plunger disposed within at least a portion of the cannula and oriented in a non-coaxial relationship with respect to the cannula; and a partial barrier disposed within the cannula adjacent to its distal end and configured to at least partially block the passageway, the partial barrier at least partially defining an object receiving opening that is in communication with the passageway and sufficiently sized to receive the object, wherein, when the device is in a first position, the partial barrier prevents the object from entering the passageway even when the plunger is inserted into the object receiving opening, wherein, when the device is moved to a second position, the passageway is aligned with the object, such that, upon movement of the plunger towards the distal end of the cannula, the plunger engages the object and pushes it through the object receiving opening towards the exit aperture.

2. The device of claim 1, wherein the movement of the device from the first position to the second position includes rotational movement of the device about the longitudinal axis of the cannula to align the object with the object receiving opening due to the effect of gravity.

3. The device of claim 1, wherein the partial barrier is crescent-shaped.

4. The device of claim 1, wherein the partial barrier is semi-circular shaped.

5. The device of claim 1, wherein the partial barrier is integral with the cannula.

6. The device of claim 1, further comprising a second partial barrier disposed within the cannula and spaced from the partial barrier towards the proximal end of the cannula to form a temporary storage space between the partial barrier and the second partial barrier, the second partial barrier at least partially defining a plunger receiving opening that is in communication with the passageway and sufficiently sized to receive the plunger, but prevent the object from entering therein.

7. The device of claim 6, wherein the second partial barrier is integral with the cannula.

8. The device of claim 1, wherein the distal end of the cannula includes a beveled tip.

9. The device of claim 1, further comprising one or more guides disposed in the cannula to guide the axial movement of the plunger within the cannula.

10. The device of claim 1, wherein the objects are spherical drug pellets.

11. A device for implanting an object into animal tissue, the device comprising:
 a cannula including first and second portions that are connectable to and separable from each other, wherein the first portion has a proximal end and an opposite distal end that is insertable into tissue and defines an exit aperture for discharge of the object from the cannula and the second portion has a proximal end and a distal end configured to connect to the proximal end of the second portion, a passageway extending from the distal end of the first portion to the proximal end of the second portion, and a longitudinal axis that extends through the first and second portions of the cannula when the first and second portions are connected together;
 an axially movable plunger disposed within at least a portion of the cannula and oriented in a non-coaxial relationship with respect to the cannula;
 a first partial barrier disposed within the first portion of the cannula and configured to at least partially block the passageway, the first partial barrier at least partially defining an object receiving opening that is in communication with the passageway and sufficiently sized to receive the object and the plunger; and
 a second partial barrier disposed within the second portion of the cannula and configured to form a temporary storage space between the first partial barrier and the second partial barrier when the first and second portions are connected together, the second partial barrier at least partially defining a plunger receiving opening that is in communication with the passageway and sufficiently sized to receive the plunger, but prevent the object from entering therein,
 wherein, when the device is in a first position, the first partial barrier prevents the object from entering the passageway even when the plunger is inserted into the object receiving opening,
 wherein, when the device is moved to a second position, the passageway is aligned with the object, such that, upon movement of the plunger towards the distal end of the first portion of the cannula, the plunger engages the object and pushes it through the object receiving opening of the first partial barrier towards the exit aperture of the first portion of the cannula.

12. The device of claim 11, wherein the movement of the device from the first position to the second position includes rotational movement of the device about the longitudinal axis of the cannula to align the object with the object receiving opening due to the effect of gravity.

13. The device of claim 11, wherein the first and second partial barriers are integral with the first and second portions of the cannula, respectively.

14. The device of claim 11, wherein the distal end of the first portion of the cannula includes a beveled tip.

15. The device of claim 11, wherein the second portion of the cannula includes one or more guides configured to guide the axial movement of the plunger within the cannula.

16. The device of claim 15, wherein the one or more guides are integral with the second portion of the cannula.

17. The device of claim 11, wherein the second portion of the cannula has a proximal end and an opposite distal end that is connectable to and separable from the proximal end of the first portion via a connector to allow objects to be loaded into the cannula.

18. The device of claim 17, wherein the connector includes a threaded connector.

19. The device of claim 17, wherein the second portion of the cannula has a proximal end and an opposite distal end that is connectable to and separable from the proximal end of the first portion via a friction fit.

20. A method for implanting an object into animal tissue, the method comprising:
 providing a device that includes:
  a cannula having a proximal end, an opposite distal end that is insertable into tissue and defines an exit aperture for discharge of the object from the cannula, and a passageway extending from the proximal end to the distal end, all of which share the same longitudinal axis;
  an axially movable plunger disposed within at least a portion of the cannula and oriented in a non-coaxial relationship with respect to the cannula; and
  a partial barrier disposed within the cannula adjacent to its distal end and configured to at least partially block the passageway, the partial barrier at least partially defining an object receiving opening that is in communication with the passageway and sufficiently sized to receive the object and the plunger,
 loading the cannula with the object;
 orienting the device to a position where the partial barrier prevents the object from entering the passageway;
 inserting the distal end of the cannula into the animal tissue;
 rotating the device about the longitudinal axis of the cannula to align the object with the object receiving opening due to the effect of gravity; and
 moving the plunger towards the distal end of the cannula to push the object through the passageway until it exits the exit aperture.

\* \* \* \* \*